United States Patent [19]
Zalkin et al.

[11] Patent Number: 5,000,173
[45] Date of Patent: Mar. 19, 1991

[54] RESPIRATORY AID DEVICE

[76] Inventors: Daniel Zalkin, 7, rue de Tournebride, 78120 Rambouillet; Daniel Isabey, 19, rue Sandrin, 94140 Alfortville; Laurent Brochard, 15, avenue Jacques Jezequel, 92170 Vanves; Alain Harf, 23 avenue de la Dame Blanche, 94120 Fontenay-sous-Bois, all of France

[21] Appl. No.: 270,614

[22] Filed: Nov. 14, 1988

[30] Foreign Application Priority Data

Nov. 19, 1987 [FR] France .................................. 87 16

[51] Int. Cl.$^5$ .......................................... A61M 16/00
[52] U.S. Cl. .......................... 128/204.21; 128/204.24; 128/205.11
[58] Field of Search ...................... 128/204.21, 204.25, 128/205.11, 204.24

[56] References Cited
FOREIGN PATENT DOCUMENTS 2414693 3/1974 Fed. Rep. of Germany .
1462182 1/1977 United Kingdom .

Primary Examiner—Edgar S. Burr
Assistant Examiner—Aaron J. Lewis
Attorney, Agent, or Firm—Curtis, Morris & Safford

[57] ABSTRACT

The device comprises a respiratory gas generator including means for establishing, during an inspiratory stage and in a supply pipe leading to an inspiratory orifice associated with an expiratory valve, a pressure of a respiratory gas which is substantially constant irrespective of the flow of inspiratory gas. The means for establishing a substantially constant pressure comprise an ejector of the convergent/divergent type which opens onto said supply pipe. In contrast to ventilators having multiple modes of ventilation which are usually intended for patients subjected to intubation or tracheomatization, the device is intended for patients who are connected to the device through a simple mask covering the nose and mouth, a nose mask or a mouthpiece.

7 Claims, 1 Drawing Sheet

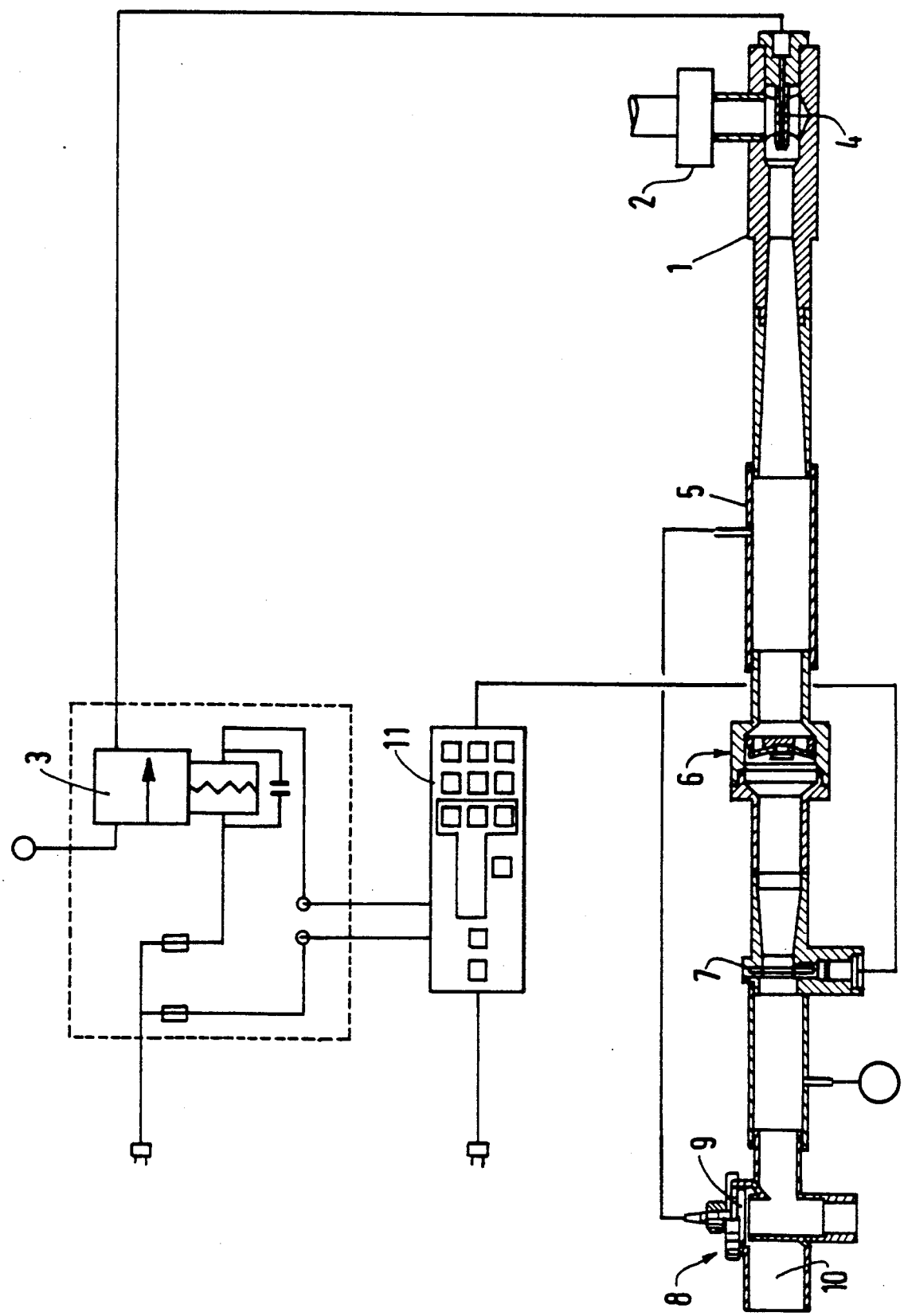

RESPIRATORY AID DEVICE

The present invention relates to a respiratory aid device intended for patients who have lost a part of their respiratory autonomy.

Devices of this type are known which comprise a respiratory gas generator including means for maintaining during an inspiratory stage, in a supply pipe leading to a respiratory orifice associated with an expiratory valve, a respiratory gas at a substantially constant pressure irrespective of the flow of the inspiratory gas.

Generally, the maintenance of a substantially constant pressure in a supply pipe leading to the respiratory orifice is ensured by a pressure-measuring means which is employed for controlling the flow of respiratory gas during the inspiratory stage. The inspiratory stage is initiated by an intake created by the patient at the beginning of the inspiration, and it terminates in a refusal of the patient at the end of the inspiration. At the end of this inspiratory stage, a usually passive expiratory stage enables the patient to empty his lungs before re-initiating a new respiratory stage.

Known devices of this type mainly comprise ventilation devices which perform the aforementioned function with the aid of relatively complex and costly means. This complexity of the means employed however permits the choice of other ventilation modes.

An object of the present invention is to provide a respiratory aid device which is exclusively adapted to aid the respiration and is simple and effective in construction and particularly cheap.

According to the invention, in the respiratory aid device of the aforementioned type, the means for establishing a substantially constant pressure comprise an ejector of the convergent-divergent type with an air inlet and an axial injecting nozzle opening out directly in the supply circuit. The supply circuit is provided with a flow sensor controlling, through an electronic signal control unit, the opening or the closure of a valve mounted between a source of gas under pressure and said axial nozzle. Advantageously, the ejector comprises a convergent part followed by a part of constant section constituting an elongated throat which opens onto a divergent diffuser. According to a particular embodiment, the throat of the ejector has a diameter of between 10 mm and 14 mm, and preferably the angle at the opening of the divergent diffuser is between 5° and 10° and preferably on the order of 7°.

The features and advantages of the invention will be apparent from the following description which is given by way of example with reference to the accompanying drawing in which the single Figure is a diagrammatic view of a device according to the invention.

BRIEF DESCRIPTION OF THE DRAWINGS

The sole drawing FIGURE is a schematic representative of a preferred embodiment of the present invention.

DETAILED DESCRIPTION OF A PREFERRED EMBODIMENT

This device comprises:

An ejector 1 provided at the air inlet with bacteriological filters 2 and receiving a supply of compressed air delivered by a source of pressure of about 3.5 bars (not shown) and determined by an electrically-operated valve 3. This supply, defined by a nozzle 4 of the ejector 1 and the available pressure, produces in the downstream circuit a pressure which is substantially constant irrespective of the total amount drawn off and adjustable between 5 and 30 mbar in accordance with the diameter of the nozzle 4 which may be varied by the choice of a nozzle from a set of nozzles of different diameters, or in any other way.

A connecting pipe 5 connecting the outlet of the ejector 1 to a check-valve 6 without resistance; the function of this valve is to prevent the return of the expirated gas and thereby avoid re-inhalation.

A hot-wire flow sensor 7 for measuring the flow of gas travelling through and employed as means for actuating and stopping the electrically-operated valve 3.

An expiratory valve 8 provided with a small inflatable gas bag 9 which closes the expiratory orifice 10 when the ejector 1 supplies gas and opens it when the ejector 1 does not supply gas, the pressure for inflating the bag being taken off on the upstream side of the check-valve.

An electronic unit 11 controlling the signal delivered by the flow sensor causes the opening of the electrically operated valve 3 when a minimum flow threshold is exceeded, which flow is produced by the intake on the part of the patient, and the closure of the valve 3 when the flow inspirated by the patient drops below a second flow threshold. These two thresholds are adjustable for the purpose of a good adaption to the requirements of the patient.

Experience has shown that the ejector 1 permits simply and effectively maintaining on the downstream side a substantially constant pressure when this ejector is supplied with gas. This ejector may have rather varied forms, but good results have been obtained with a divergent diffuser on the order of 7° with a nozzle throat on the order 0.8 to 1.2 mm.

The fields of application are the following:

In contrast to the ventilators having multiple modes of ventilation which are generally intended for patients subjected to intubation or tracheotomization, the invention is intended for patients who are connected to the device by means of a simple mask covering the nose and mouth, a nose mask or a mouthpiece.

The source of pressure may be the circuit distributing medical air in a hospital or a small compressor provided with filters adapted to the production of breathable air.

The population of patients who may benefit from this technique is principally represented by post-operated patients and patients having chronic respiratory insufficiencies.

I claim:

1. A respiratory aid device comprising a respiratory aid gas generator for fluid connection between a source of gas under pressure and a patient valve having an inspiratory inlet associated with an expiratory valve, said gas generator comprising:

a gas supply pipe connectable to said inspiratory inlet and provided with a flow sensor;

a convergent/divergent ejector having an air inlet and a coaxially arranged injecting nozzle opening into said supply pipe, upstream said flow sensor and in fluid connection with said source of gas under pressure;

an electrically controllable valve for connecting said source of gas under pressure with said ejector; and an electronic control unit responsive to signals from said flow sensor to selectively actuate said electrically controllable valve, whereby respiratory gas at a selectable substantially constant pressure is supplied to said patient valve during an inspiratory phase.

2. A respiratory aid device according to claim 1, wherein the ejector comprises a convergent part, a throat having a constant diameter and following on said convergent part, and a divergent diffuser following on said throat relative to the direction of flow through said ejector.

3. A respiratory aid device according to claim 2, wherein the throat has a diameter on the order of 10 to 14 mm.

4. A respiratory aid device according to claim 2, wherein the divergent diffuser has an angle of between 5° and 10°.

5. A respiratory aid device according to claim 4, wherein said angle is on the order of 7°.

6. A respiratory aid device according to claim 2, wherein the nozzle is interchangeable in accordance with the desired aid pressure and defines a passage whose diameter is between 0.8 and 1.2 mm, said respiratory gas being introduced in the ejector through said interchangeable nozzle.

7. The device of claim 1, further comprising a non-return valve in the supply pipe between said flow sensor and said ejector.

* * * * *

UNITED STATES PATENT AND TRADEMARK OFFICE
CERTIFICATE OF CORRECTION

PATENT NO. : 5,000,173

DATED : March 19, 1991

INVENTOR(S) : Daniel Zalkin, Daniel Isabey, Laurent Brochard and Alain Harf

It is certified that error appears in the above-identified patent and that said Letters Patent is hereby corrected as shown below:

On the title page, please insert item [73] Assignee:

-- L'AIR LIQUIDE, SOCIETE ANONYME POUR L'ETUDE
ET L'EXPLOITATION DES PROCEDES GEORGES CLAUDE
and
INSTITUT NATIONAL DE LA SANTE ET DE LA RECHERCHE
MEDICALE, BOTH OF PARIS, FRANCE --.

Signed and Sealed this

Twentieth Day of October, 1992

Attest:

DOUGLAS B. COMER

*Attesting Officer*    *Acting Commissioner of Patents and Trademarks*